(12) United States Patent
Black et al.

(10) Patent No.: US 11,841,310 B2
(45) Date of Patent: Dec. 12, 2023

(54) FLOW CELLS AND SEQUENCING KITS

(71) Applicant: ILLUMINA, INC., San Diego, CA (US)

(72) Inventors: Hayden Black, San Diego, CA (US); Brian D. Mather, San Diego, CA (US)

(73) Assignee: Illumina, Inc., San Diego, CA (US)

(*) Notice: Subject to any disclaimer, the term of this patent is extended or adjusted under 35 U.S.C. 154(b) by 0 days.

(21) Appl. No.: 16/701,863

(22) Filed: Dec. 3, 2019

(65) Prior Publication Data

US 2020/0191699 A1    Jun. 18, 2020

Related U.S. Application Data

(60) Provisional application No. 62/780,602, filed on Dec. 17, 2018.

(51) Int. Cl.
| | | |
|---|---|---|
| *G01N 15/14* | (2006.01) | |
| *C12Q 1/6869* | (2018.01) | |
| *B01L 3/00* | (2006.01) | |

(52) U.S. Cl.
CPC ....... *G01N 15/1404* (2013.01); *C12Q 1/6869* (2013.01); *B01L 3/502715* (2013.01);
(Continued)

(58) Field of Classification Search
CPC .............. G01N 15/1404; C12Q 1/6869; C12Q 2565/607; C12Q 2563/103;
(Continued)

(56) References Cited

U.S. PATENT DOCUMENTS 5,786,141 A * 7/1998 Bard ...................... C12Q 1/005
435/5
6,316,180 B1   11/2001 Martin
(Continued)

FOREIGN PATENT DOCUMENTS

| EA | 001198 B1 | 12/2000 |
|---|---|---|
| EP | 2576065 B1 | 12/2018 |

(Continued)

OTHER PUBLICATIONS

Guo et al. (Accounts of chemical research, vol. 43, No. 4, 551-563). (Year: 2010).*

(Continued)

*Primary Examiner* — Benjamin R Whatley
(74) *Attorney, Agent, or Firm* — Dierker & Kavanaugh, P.C.

(57) ABSTRACT

In one example, a flow cell includes a substrate, an electrode positioned on the substrate, and a patterned material positioned on the electrode. In this example, the patterned material includes depressions separated by interstitial regions, and a functionalized surface of the electrode is exposed at each of the depressions. In this example, the flow cell further includes a primer grafted to the functionalized surface in each of the depressions. In another example, a flow cell includes a substrate and a patterned electrode positioned on the substrate. In this other example, the patterned electrode includes depressions separated by interstitial regions, and a functionalized surface of the substrate exposed at each of the depressions. In this other example, a primer is grafted to the functionalized surface in each of the depressions.

10 Claims, 5 Drawing Sheets

(52) U.S. Cl.
CPC ............... *B01L 2300/0645* (2013.01); *B01L 2300/0877* (2013.01); *B01L 2300/0893* (2013.01)

(58) Field of Classification Search
CPC ....... B01L 2300/0893; B01L 3/502715; B01L 2300/0877; B01L 2300/0645
See application file for complete search history.

(56) References Cited

U.S. PATENT DOCUMENTS

| | | | |
|---|---|---|---|
| 6,569,382 | B1 | 5/2003 | Edman et al. |
| 9,891,221 | B2 | 2/2018 | Tsionsky et al. |
| 2004/0249227 | A1 | 12/2004 | Klapproth et al. |
| 2005/0019803 | A1 | 1/2005 | Liu et al. |
| 2006/0257560 | A1* | 11/2006 | Barone ............... C03C 17/328 427/240 |
| 2009/0317917 | A1* | 12/2009 | Klapproth ............ B82Y 30/00 436/172 |
| 2011/0203924 | A1* | 8/2011 | Wohlstadter ........... G01N 21/76 204/403.01 |
| 2016/0318016 | A1* | 11/2016 | Hou ................ B01L 3/502715 |
| 2018/0195950 | A1 | 7/2018 | Tsay et al. |
| 2020/0055046 | A1* | 2/2020 | Reed ................ G01N 35/1095 |

FOREIGN PATENT DOCUMENTS

| | | |
|---|---|---|
| JP | 2004534226 A | 11/2004 |
| JP | 2005512022 A | 4/2005 |
| JP | 2016525466 A | 8/2016 |
| JP | 2017503483 A | 2/2017 |
| WO | 1996028538 A1 | 9/1996 |
| WO | 9828320 A2 | 7/1998 |
| WO | 20030018889 A2 | 1/2003 |
| WO | 2014122548 A2 | 8/2014 |
| WO | 2015002813 A1 | 1/2015 |
| WO | 2015100373 A2 | 7/2015 |

OTHER PUBLICATIONS

Chen, S., et al., "Highly Sensitive and Quality Self-Testable Electrochemiluminescence Assay of DNA Methyltransferase Activity Using Multifunctional Sandwich-Assembled Carbon Nitride Nanosheets", ACS Appl. Mater. Interfaces, 10, 2018, 6887-6894.

Chow, B., et al., "Photoelectrochemical synthesis of DNA microarrays", Proceedings of the National Academy of Sciences, vol. 106, No. 36, Sep. 8, 2009, 15219-15224.

Lu, Q., et al., "Cathodic electrochemiluminescence behavior of an ammonolysis product of 3,4,9,10-perylenetetracarboxylic dianhydride in aqueous solution and its application for detecting dopamine", RSC Advances, 5, 2015, 22289-22293.

Xu, J., et al., "Analysis of Intracellular Glucose at Single Cells Using Electrochemiluminescence Imaging", Anal. Chem. 88, 2016, 4609-4612.

Zhang, J., et al., "Electrochemiluminescence behavior of meso-tetra (4-sulfonatophenyl)porphyrin in aqueous medium: its application for highly selective sensing of nanomolar $Cu^{2+}$", Anal. Bioanal. Chem., Jun. 17, 2016.

* cited by examiner

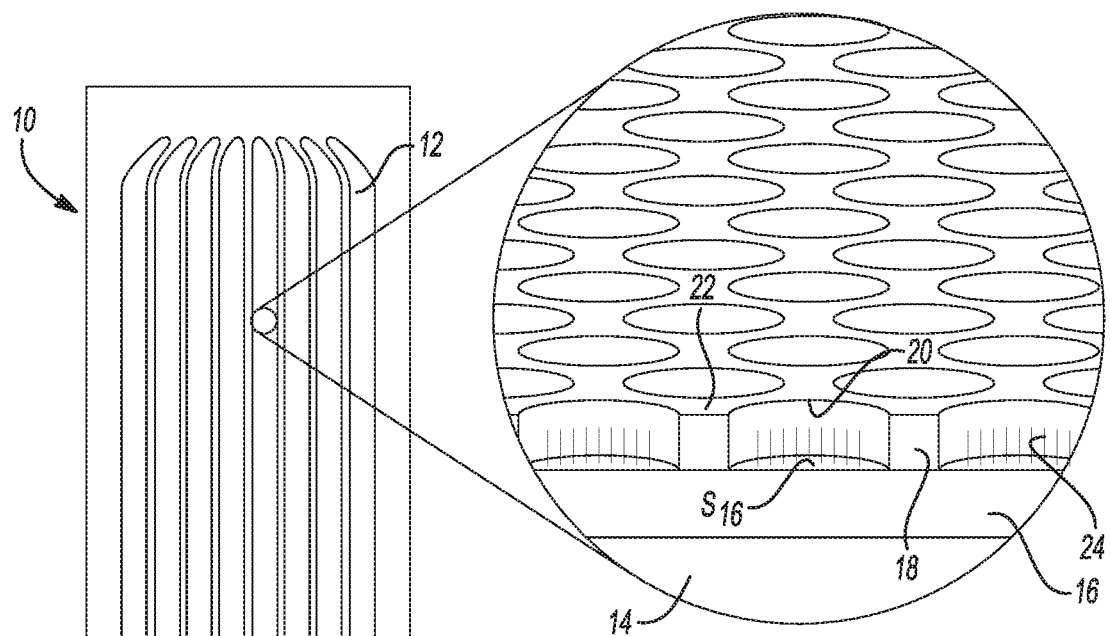
*Fig-1B*
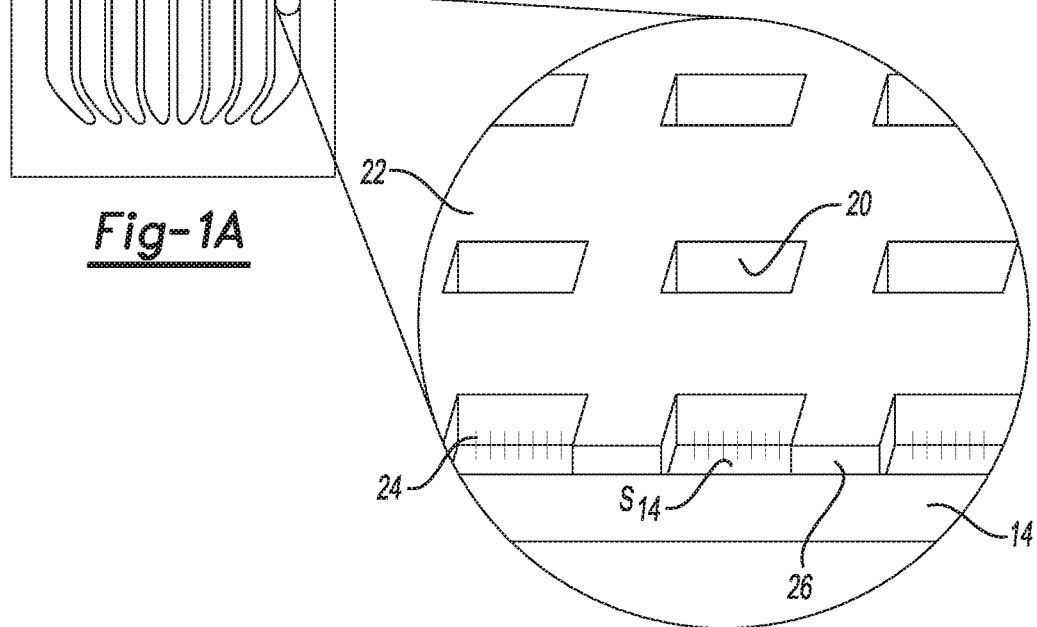
*Fig-1A*
*Fig-1C*

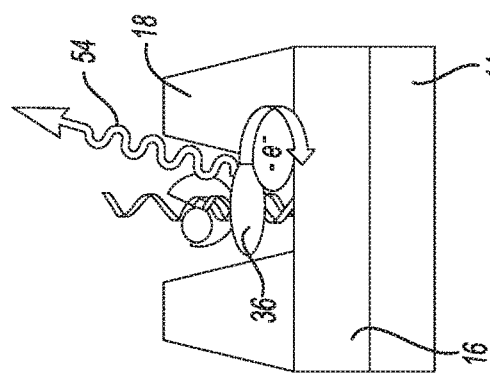
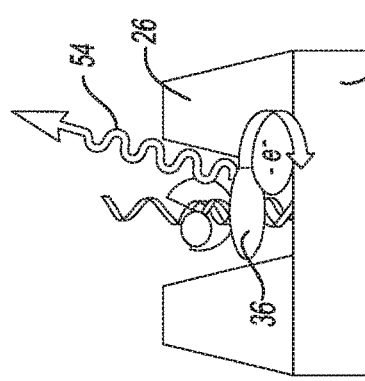
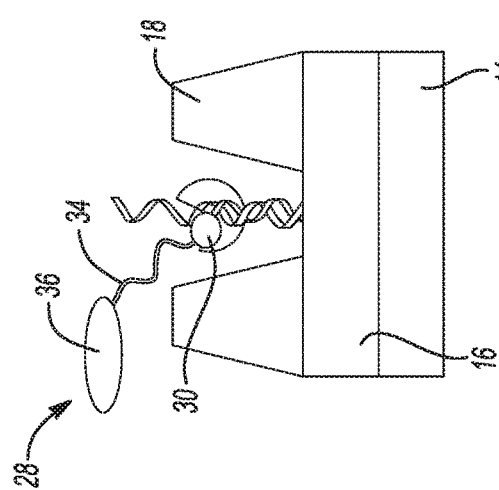
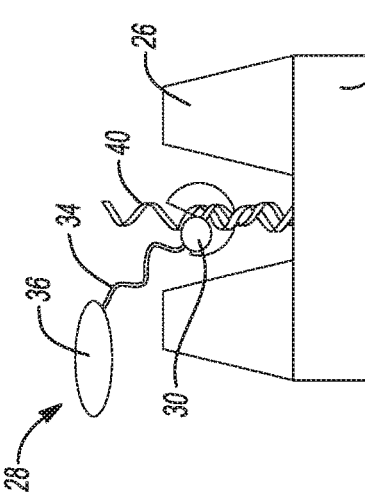
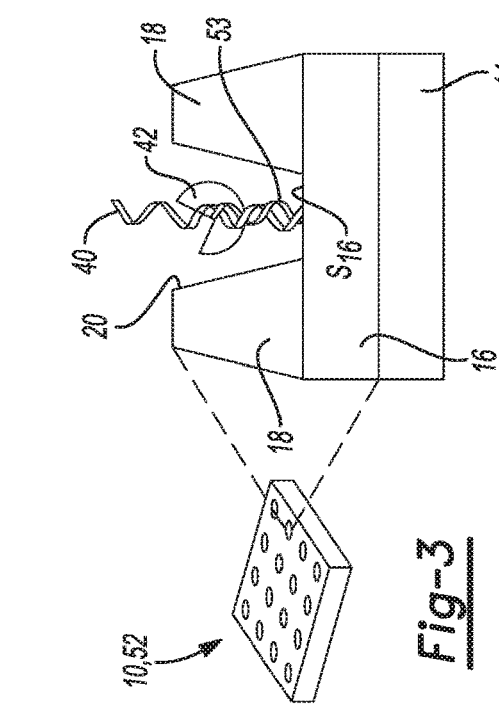
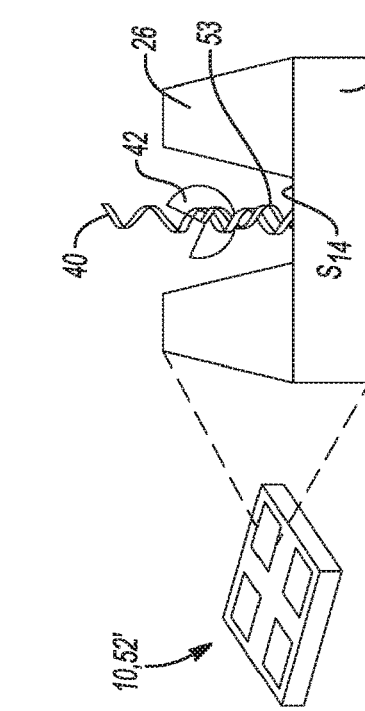

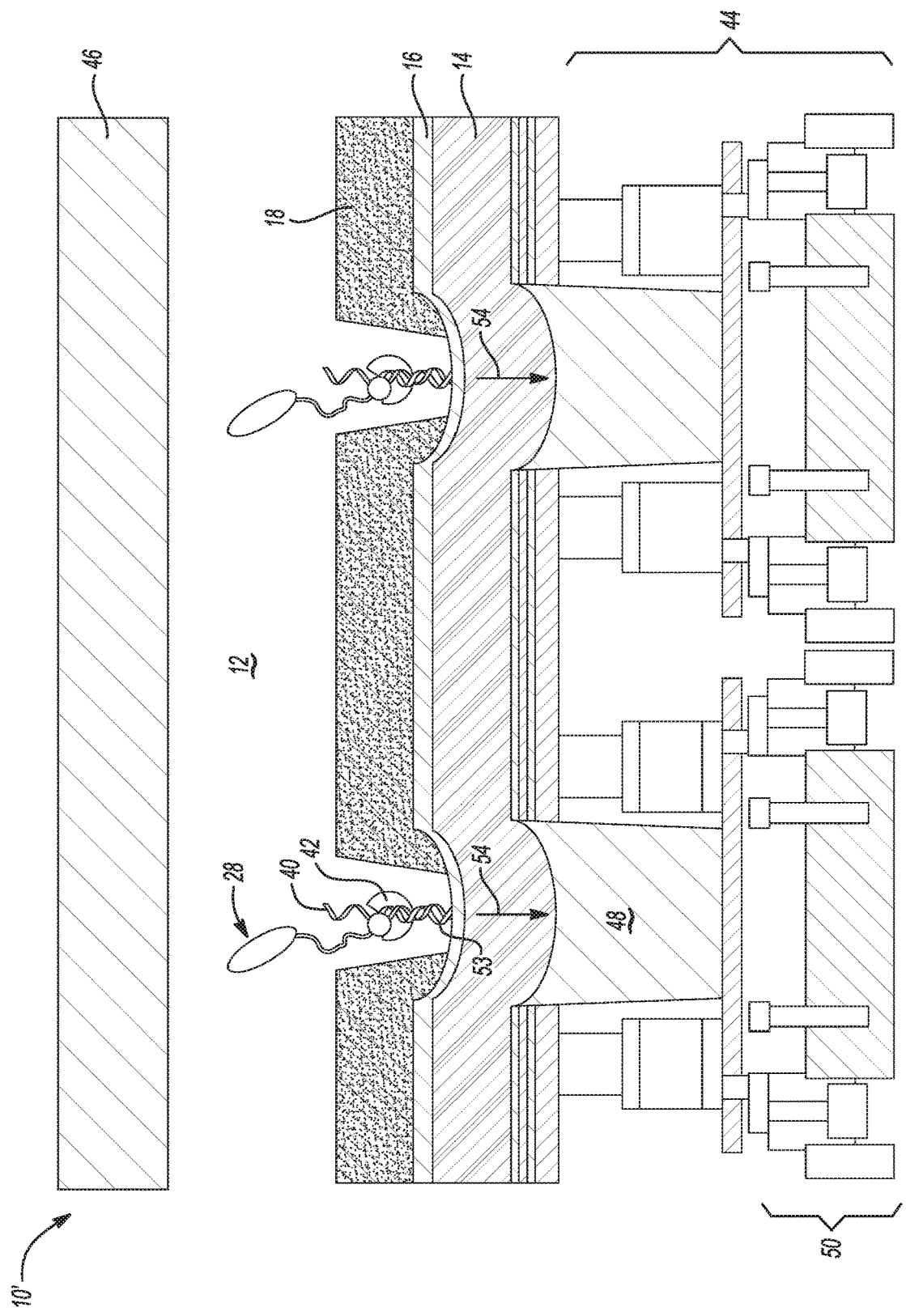

FLOW CELLS AND SEQUENCING KITS

CROSS-REFERENCE TO RELATED APPLICATION

This application claims the benefit of U.S. Provisional Application Ser. No. 62/780,602, filed Dec. 17, 2018; the content of which is incorporated by reference herein in its entirety.

BACKGROUND

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. For example, in some multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing. With polynucleotide sequencing techniques, the analysis may help identify or reveal properties of the polynucleotide involved in the reactions.

INTRODUCTION

A first aspect disclosed herein is a first flow cell comprising a substrate; an electrode positioned on the substrate; a patterned material positioned on the electrode, the patterned material including depressions separated by interstitial regions; a functionalized surface of the electrode exposed at each of the depressions; and a primer grafted to the functionalized surface in each of the depressions.

In an example of the first aspect, the electrode includes gold and the functionalized surface includes thiol linkers or amine linkers; or the electrode includes indium tin oxide and the functionalized surface includes a silane linker.

In an example of the first aspect, the electrode is transparent; the substrate is transparent; and the flow cell further comprises a detection device in contact with the substrate, the detection device including a respective photodiode operatively associated with each of the depressions and device circuitry electrically connected to the respective photodiode.

It is to be understood that any features of the first flow cell disclosed herein may be combined together in any desirable manner and/or configuration.

A second aspect disclosed herein is a sequencing kit comprising the flow cell as defined in the first aspect and labeled nucleotides to be introduced into the flow cell, each labeled nucleotide including a nucleotide having a 3' OH blocking group, a linking molecule attached to a base or a sugar of the nucleotide, and an electrochemiluminescent label attached to the linking molecule.

In an example of the second aspect, the labeled nucleotides include at least three different labeled nucleotides, and wherein a respective electrochemiluminescent label of each of the at least three different labeled nucleotides has a distinct emission spectrum.

In an example of the second aspect, the labeled nucleotides include at least three different labeled nucleotides, and wherein a respective electrochemiluminescent label of each of the at least three different labeled nucleotides has a distinct oxidation or reduction potential.

In an example of the second aspect, the labeled nucleotides include at least three different labeled nucleotides, and wherein a respective electrochemiluminescent label of each of the at least three different labeled nucleotides has a distinct lifetime for electrochemiluminescence emission.

In an example of the second aspect, the labeled nucleotides include at least three different labeled nucleotides, and wherein a respective electrochemiluminescent label of each of the at least three different labeled nucleotides has a distinct electrochemiluminescence emission intensity.

It is to be understood that any features of this sequencing kit may be combined together in any desirable manner. Moreover, it is to be understood that any combination of features of this sequencing kit and/or of the flow cell may be used together, and/or combined with any of the examples disclosed herein.

A third aspect disclosed herein is another flow cell comprising a substrate, a patterned electrode positioned on the substrate, the patterned electrode including depressions separated by interstitial regions, a functionalized surface of the substrate exposed at each of the depressions, and a primer grafted to the functionalized surface in each of the depressions.

In an example of the third aspect, the functionalized surface of the substrate includes a polymer layer attached to silane groups attached to the substrate.

In an example of the third aspect, the functionalized surface of the substrate includes hydroxyl groups attached to the substrate.

In an example of the third aspect, the substrate is transparent; and the flow cell further comprises a detection device in contact with the substrate, the detection device including a respective photodiode operatively associated with each of the depressions; and device circuitry electrically connected to the respective photodiode.

It is to be understood that any features of this flow cell may be combined together in any desirable manner. Moreover, it is to be understood that any combination of features of this flow cell and/or of the sequencing kit and/or of the other flow cell may be used together, and/or combined with any of the examples disclosed herein.

A fourth aspect disclosed herein is an sequencing kit, comprising the flow cell as defined in the third aspect, and labeled nucleotides to be introduced into the flow cell, each labeled nucleotide including a nucleotide having a 3' OH blocking group, a linking molecule attached to a base or a sugar of the nucleotide, and an electrochemiluminescent label attached to the linking molecule.

In an example of the fourth aspect, the labeled nucleotides include at least three different labeled nucleotides, and wherein a respective electrochemiluminescent label of each of the at least three different labeled nucleotides has a distinct emission spectrum.

In an example of the fourth aspect, the labeled nucleotides include at least three different labeled nucleotides, and wherein the electrochemiluminescent label of each of the at least three different labeled nucleotides has a distinct oxidation or reduction potential.

In an example of the fourth aspect, the labeled nucleotides include at least three different labeled nucleotides, and wherein a respective electrochemiluminescent label of each of the at least three different labeled nucleotides has a distinct lifetime for electrochemiluminescence emission.

In an example of the fourth aspect, the labeled nucleotides include at least three different labeled nucleotides, and wherein a respective electrochemiluminescent label of each of the at least three different labeled nucleotides has a distinct electrochemiluminescence emission intensity.

It is to be understood that any features of this sequencing kit may be combined together in any desirable manner. Moreover, it is to be understood that any combination of features of this sequencing kit and/or of either of the flow cells and/or the other sequencing kit may be used together, and/or combined with any of the examples disclosed herein.

A fifth aspect disclosed herein is a method comprising: introducing a fluid including a polymerase and nucleotides to a flow cell including an electrode that partially defines a depression including a template polynucleotide chain attached in the depression, wherein at least some of the nucleotides are labeled nucleotides, each of the at least some labeled nucleotides including a nucleotide having a 3' OH blocking group, a linking molecule attached to a base or a sugar of the nucleotide, and an electrochemiluminescent label attached to the linking molecule, whereby one of the nucleotides incorporates into a nascent strand complementary to the template polynucleotide chain; applying a potential to the electrode; and detecting an optical emission in response to the applied potential.

In an example of the fifth aspect, the incorporated one of the nucleotides is one of the labeled nucleotides, and wherein the application of the potential initiates a redox reaction pathway involving the electrochemiluminescent label of the incorporated one of the labeled nucleotides. In one example, the fluid includes at least three different labeled nucleotides, a respective electrochemiluminescent label of each of the at least three different labeled nucleotides has a distinct emission spectrum, and the method further comprises identifying the incorporated one of the labeled nucleotides from its optical emission. In another example, the fluid includes at least three different labeled nucleotides, a respective electrochemiluminescent label of each of the at least three different labeled nucleotides has a distinct oxidation or reduction potential, and the method further comprises identifying the incorporated one of the labeled nucleotides from the applied potential. In still another example, prior to applying the potential, the method further comprises introducing a co-reactant to the flow cell. In yet a further example, the linking molecule and electrochemiluminescent label of the incorporated one of the labeled nucleotides are attached during incorporation, potential application, and optical detection, and wherein after the optical detection, the method further comprises introducing a de-blocking agent to cleave the linking molecule and the electrochemiluminescent label from the incorporated one of the labeled nucleotides and to remove the 3' OH blocking group from the incorporated one of the labeled nucleotides, thereby enabling incorporation of another nucleotide or another labeled nucleotide into a nascent strand. In this particular example, the method may further comprise introducing another fluid, applying another potential to the electrode, and detecting another optical emission.

In an example of the fifth aspect, a photodiode detects the optical emission, and the method further comprises detecting an electrical signal that corresponds to the optical emission.

In an example of the fifth aspect, the incorporated one of the nucleotides is one of: a first labeled nucleotide, wherein the linking molecule is cleavable; a second labeled nucleotide, wherein the linking molecule is non-cleavable; a third non-labeled nucleotide having a 3' OH blocking group and including a linking molecule that is to attach to the electrochemiluminescent label; or a fourth non-labeled nucleotide having a 3' OH blocking group; and the method further comprises introducing a reagent that can cleave the electrochemiluminescent label from the first labeled nucleotide and can add the electrochemiluminescent label to the third non-labeled nucleotide, applying another potential to the electrode, detecting another optical emission in response to the applied potential, and using the detected optical emission and the detected other optical emission to identify the incorporated one of the nucleotides.

In an example of the fifth aspect, the flow cell includes a plurality of depressions, each of which includes a plurality of template polynucleotide chains attached in the depression, a respective one of the nucleotides incorporates into a respective nascent strand complementary to the respective template polynucleotide chain, and the method further comprises simultaneously detecting a respective optical emission from each of the plurality of depressions.

It is to be understood that any features of the method may be combined together in any desirable manner. Moreover, it is to be understood that any combination of features of the method and/or of the first sequencing kit and/or of the second sequencing kit may be used together, and/or combined with any of the examples disclosed herein.

Still further, it is to be understood that any features of any of the methods and/or of any of the sequencing kits may be combined together in any desirable manner, and/or may be combined with any of the examples disclosed herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 1A is a top view of an example of a flow cell;

FIG. 1B is an enlarged, perspective view of an example of a portion of one of the flow cell lanes of FIG. 1A, illustrating depressions defined on an electrode surface and primers attached on the electrode surface in the depression;

FIG. 1C is an enlarged, perspective view of another example of a portion of one of the flow cell lanes of FIG. 1A, illustrating depressions defined by a patterned electrode on a substrate surface and primers attached on the substrate surface in the depressions;

FIG. 3 is a semi-schematic perspective view of one example of an array of depressions of a flow cell for a sequencing kit;

FIGS. 4A through 4C depict a cross-sectional view of one depression of the array of FIG. 3 as it is exposed to a sequencing cycle;

FIG. 5 is a semi-schematic perspective view of another example of an array of depressions of a flow cell for a sequencing kit;

FIGS. 6A through 6C depict a cross-sectional view of one depression of the array of FIG. 5 as it is exposed to a sequencing cycle;

FIG. 7 is a cross-sectional view of an example of a flow cell for a sequencing kit, where the flow cell incorporates a complementary metal-oxide semiconductor (CMOS) detection device.

DETAILED DESCRIPTION

Figure 2:
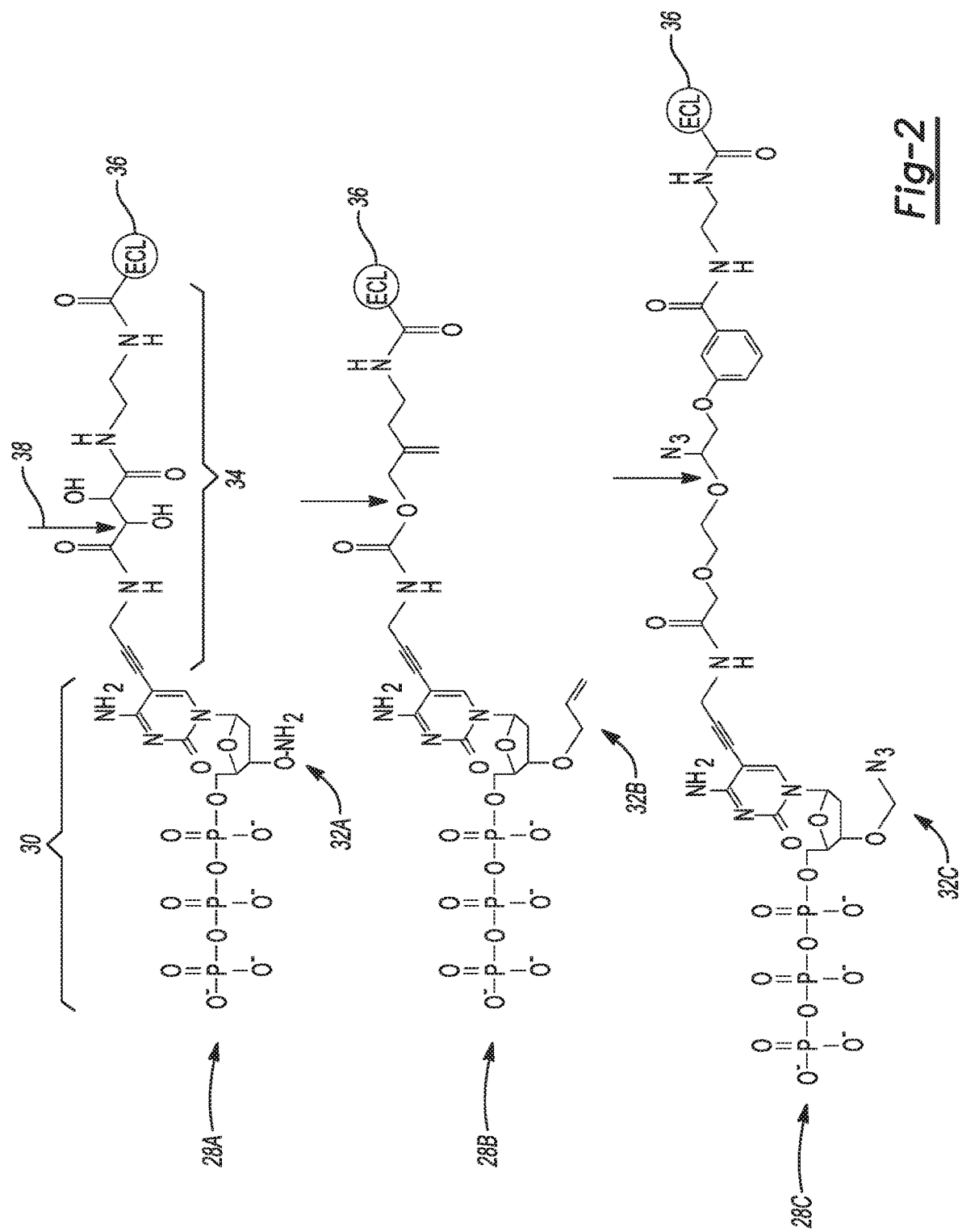
FIG. 2 schematically depicts different examples of a labeled nucleotide.

In the examples disclosed herein, nucleotide base calling during sequencing is performed via detection of fluorescence signals that are generated electrochemically. Electrochemical generation of the fluorescence signals does not involve excitation of dye-labeled bases through illumination with a laser, light emitting diode, or other illumination source. Without the need for an excitation source, the optical system of the examples disclosed herein is simplified.

The process of electrochemiluminescence (ECL) begins with the oxidation or reduction of a molecule at an electrode surface to form a radical cation or anion. In some examples, the radical cation or anion then undergoes electron transfer with a co-reactant to form an emissive excited state. In other examples, the potential of the electrode is swept from positive to negative, which can directly generate the emissive excited state. In either example, the process disclosed herein produces light with no background noise from the excitation source. As such, the examples disclosed herein eliminate noise due to the excitation source, and thus increase the signal to noise ratio. An increased signal to noise ratio improves sequencing accuracy, and also enables smaller pitch to be used due to the higher data density.

Additionally, in the examples disclosed herein, the excited states are formed exclusively at the electrode surface or within a depression that is defined by electrode walls, which facilitates spatially resolved ECL active areas.

Still further, the number of photons that are emitted depends on the efficiency of the ECL reaction and the duration of the applied potential. In theory, an ECL active molecule can undergo numerous redox/reaction/emission cycles and can emit photons for the duration of applied potential. This enables the time frame for signal generation to be adjusted, which may lead to more accurate detection results.

In the examples disclosed herein, the signals are electrochemically generated using sequencing kits. An example of the sequencing kit described herein is an electrochemiluminescence sequencing kit. Although electrochemiluminescence sequencing kits are used herein as a representative example of a sequencing kit, a sequencing kit herein need not be an electrochemiluminescence kit. Each electrochemiluminescence sequencing kit includes a specific flow cell that incorporates the electrode to be used in the ECL process. In some examples, the flow cells may be used with an optical detection device. In other examples, the flow cells are integrated with a complementary metal-oxide semiconductor (CMOS) detection device, and thus are used for optoelectronic detection.

An example of the flow cell 10 is depicted in FIG. 1A. In this example, the flow cell 10 includes flow channels 12. While several flow channels 12 are shown, it is to be understood that any number of channels 12 may be included in the flow cell 10 (e.g., a single channel 12, four channels 12, etc.). Each flow channel 12 is an area defined between two bonded components (e.g., a substrate and a lid or two substrates), which can have liquids introduced thereto and removed therefrom. Each flow channel 12 may be isolated from each other flow channel 12 so that liquid introduced into any particular flow channel 12 does not flow into any adjacent flow channel. As will be discussed further herein, the liquids introduced into the flow channels 12 may introduce reaction components (e.g., labeled and/or non-labeled nucleotides), washing solutions, deblocking agents, etc.

Different examples of the architecture within the flow channels 12 of the flow cell 10 are shown in FIGS. 1B and 1C.

In the example shown in FIG. 1B, the flow cell 10 includes a substrate 14, an electrode 16 positioned on the substrate 14, and a patterned material 18 positioned on the electrode 16. The patterned material 18 defines depressions 20 separated by interstitial regions 22. In this example, a functionalized surface S16 of the electrode 16 is exposed at each of the depressions 20, and a primer 24 is grafted to the functionalized surface S16.

The substrate 14 in FIG. 1B provides support for the other components of the flow cell 10. The substrate 14 is generally rigid and is insoluble in an aqueous liquid. Examples of suitable substrates 14 include epoxy siloxane, glass, modified glass, plastics, nylon, ceramics/ceramic oxides, silica (silicon oxide ($SiO_2$)), fused silica, silica-based materials, aluminum silicate, silicon, modified silicon (e.g., boron doped p+ silicon), silicon nitride ($Si_3N_4$), tantalum pentoxide ($TaO_5$) or other tantalum oxide(s) ($TaO_x$), hafnium oxide ($HaO_2$), inorganic glasses, or the like. Some examples of suitable plastics for the substrate 14 include acrylics, polystyrene, copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc. The support may also be glass or silicon, with a coating layer of tantalum oxide or another ceramic oxide at the surface.

The form of the substrate 14 may be a wafer, a panel, a rectangular sheet, a die, or any other suitable configuration. In an example, the substrate 14 may be a circular wafer or panel having a diameter ranging from about 2 mm to about 300 mm. As a more specific example, the substrate 14 is a wafer having a diameter ranging from about 200 mm to about 300 mm. In another example, the substrate 14 may be a rectangular sheet or panel having its largest dimension up to about 10 feet (~3 meters). As a specific example, the support 14 is a die having a width ranging from about 0.1 mm to about 10 mm. While example dimensions have been provided, it is to be understood that a substrate 14 with any suitable dimensions may be used.

In FIG. 1B, the electrode 16 is positioned on the substrate 12. The electrode 16 may include any suitable electrode material, such as gold (Au), silver (Ag), silver chloride (AgCl), platinum (Pt), titanium (Ti), molybdenum (Mo), indium tin oxide (ITO), indium zin oxide (IZO), carbon (e.g., graphene, carbon nanotube sheets), conductive polymers, etc. In an example, the electrode 16 is gold. The electrode 16 may have any suitable thickness that renders the electrode 16 mechanically and chemically stable. As an example, the thickness may be 200 nm or more.

The electrode 16 may be a preformed sheet that is attached to the substrate 14, e.g., using an adhesive, or may be deposited on the substrate 12 using a suitable deposition technique.

In the example shown in FIG. 1B, the patterned material 18 is positioned on the electrode 16. It is to be understood that any material that can be selectively deposited, or deposited and patterned to form the depressions 20 and the interstitial regions 22 may be used for the patterned material 18. The patterned material 18 may be conductive or non-conductive, and is selected so that it does not graft the primers 24.

As one example, an inorganic oxide may be selectively applied to the electrode 16 via vapor deposition, aerosol printing, or inkjet printing. Examples of suitable inorganic oxides include tantalum oxide, aluminum oxide, silicon oxide, hafnium oxide, etc.

As another example, a resin may be applied to the electrode 16 and then patterned. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, printing techniques, etc. Some examples of suitable resins include a polyhedral oligomeric silsesquioxane resin (POSS)-based resin, a non-POSS epoxy resin, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

As used herein, the term "polyhedral oligomeric silsesquioxane" (POSS) refers to a chemical composition that is a hybrid intermediate (e.g., $RSiO_{1.5}$) between that of silica ($SiO_2$) and silicone ($R_2SiO$). An example of POSS can be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for POSS include epoxy, azide/azido, a thiol, a poly(ethylene glycol), a norbornene, a tetrazine, acrylates, and/or methacrylates, or further, for example, alkyl, aryl, alkoxy, and/or haloalkyl groups. The resin composition disclosed herein may comprise one or more different cage or core structures as monomeric units. The polyhedral structure may be a $T_8$ structure, such as:

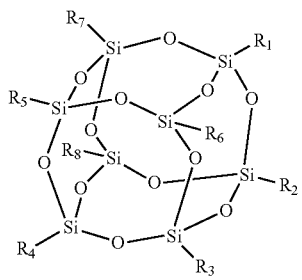

and represented by:

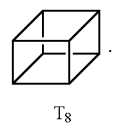

$T_8$

This monomeric unit typically has eight arms of functional groups $R_1$ through $R_8$.

The monomeric unit may have a cage structure with 10 silicon atoms and 10 R groups, referred to as $T_{10}$, such as:

$T_{10}$ or may have a cage structure with 12 silicon atoms and 12 R groups, referred to as $T_{12}$, such as:

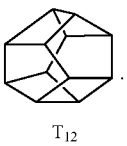

$T_{12}$

The POSS-based material may alternatively include $T_6$, $T_{14}$, or $T_{16}$ cage structures. The average cage content can be adjusted during the synthesis, and/or controlled by purification methods, and a distribution of cage sizes of the monomeric unit(s) may be used in the examples disclosed herein.

As shown in FIG. 1B, the patterned material 18 includes the depressions 20 defined therein, and interstitial regions 22 separating adjacent depressions 20. Many different layouts of the depressions 20 may be envisaged, including regular, repeating, and non-regular patterns. In an example, the depressions 20 are disposed in a hexagonal grid for close packing and improved density. Other layouts may include, for example, rectilinear (i.e., rectangular) layouts, triangular layouts, and so forth. In some examples, the layout or pattern can be an x-y format of depressions 20 that are in rows and columns. In some other examples, the layout or pattern can be a repeating arrangement of depressions 20 and/or interstitial regions 22. In still other examples, the layout or pattern can be a random arrangement of depressions 20 and/or interstitial regions 22. The pattern may include spots, pads, wells, posts, stripes, swirls, lines, triangles, rectangles, circles, arcs, checks, plaids, diagonals, arrows, squares, and/or cross-hatches.

The layout or pattern of the depressions 20 may be characterized with respect to the density of the depressions 20 (i.e., number of depressions 20) in a defined area. For example, the depressions 20 may be present at a density of approximately 2 million per $mm^2$. The density may be tuned to different densities including, for example, a density of about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more, or less. It is to be further understood that the density of depressions 20 in the patterned material 18 can be between one of the lower values and one of the upper values selected from the ranges above. As examples, a high density array may be characterized as having depressions 20 separated by less than about 100 nm, a medium density array may be characterized as having depressions 20 separated by about 400 nm to about 1 μm, and a low density array may be characterized as having depressions 20 separated by greater than about 1 μm. While example densities have been provided, it is to be understood that any suitable densities may be used.

The layout or pattern of the depressions 20 may also or alternatively be characterized in terms of the average pitch, i.e., the spacing from the center of the depression 20 to the center of an adjacent depression 20 (center-to-center spacing) or from the edge of one depression 20 to the edge of an adjacent depression 20 (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.1 µm, about 0.5 µm, about 1 µm, about 5 µm, about 10 µm, about 100 µm, or more or less. The average pitch for a particular pattern of depressions 20 can be between one of the lower values and one of the upper values selected from the ranges above. In an example, the depressions 20 have a pitch (center-to-center spacing) of about 1.5 µm. While example average pitch values have been provided, it is to be understood that other average pitch values may be used.

The size of each depression 20 may be characterized by its volume, opening area, depth, and/or diameter.

Each depression 20 can have any volume that is capable of confining a liquid. The minimum or maximum volume can be selected, for example, to accommodate the throughput (e.g., multiplexing), resolution, analyte composition, or analyte reactivity expected for downstream uses of the flow cell 10. For example, the volume can be at least about $1 \times 10^{-3}$ µm$^3$, about $1 \times 10^{-2}$ µm$^3$, about 0.1 µm$^3$, about 1 µm$^3$, about 10 µm$^3$, about 100 µm$^3$, or more. Alternatively or additionally, the volume can be at most about $1 \times 10^4$ µm$^3$, about $1 \times 10^3$ µm$^3$, about 100 µm$^3$, about 10 µm$^3$, about 1 µm$^3$, about 0.1 µm$^3$, or less.

The area occupied by each depression opening can be selected based upon similar criteria as those set forth above for the volume. For example, the area for each depression opening can be at least about $1 \times 10^{-3}$ µm$^2$, about $1 \times 10^{-2}$ µm$^2$, about 0.1 µm$^2$, about 1 µm$^2$, about 10 µm$^2$, about 100 µm$^2$, or more. Alternatively or additionally, the area can be at most about $1 \times 10^3$ µm$^2$, about 100 µm$^2$, about 10 µm$^2$, about 1 µm$^2$, about 0.1 µm$^2$, about $1 \times 10^{-2}$ µm$^2$, or less. The area occupied by each depression opening can be greater than, less than or between the values specified above.

The depth of each depression 20 can be at least about 0.1 µm, at least about 0.5 µm, at least about 1 µm, at least about 10 µm, at least about 100 µm, or more. Alternatively or additionally, the depth can be at most about $1 \times 10^3$ µm, at most about 100 µm, at most about 10 µm, at most about 1 µm, at most about 0.1 µm, or less. In some examples, the depth is about 0.4 µm. The depth of each depression 20 can be greater than, less than or between the values specified above.

In some instances, the diameter or length and width of each depression 20 can be at least about 50 nm, about 0.1 µm, about 0.5 µm, about 1 µm, about 10 µm, about 100 µm, or more. Alternatively or additionally, the diameter or length and width can be at most about $1 \times 10^3$ µm, about 100 µm, about 10 µm, about 1 µm, about 0.5 µm, about 0.1 µm, or less (e.g., about 50 nm). The diameter or length and width may also vary along the depth (e.g., as shown in FIGS. 4A-4C and 6A-6C). The diameter or length and width of each depression 20 can be greater than, less than or between the values specified above.

In the example shown in FIG. 1B, the surface $S_{16}$ of the electrode 16 exposed at the depressions 20 is functionalized so that primers 24 can attach to the surface $S_{16}$ and not to the interstitial regions 22. The functionalization of the electrode surface $S_{16}$ will depend on the material of the electrode and the primer 24 that is to be attached thereto.

In some examples, the electrode material may be inherently functionalized because the primer 24 includes a terminal functional group that can directly attach to the unmodified electrode material. For examples, a thiol terminated primer may chemically bond to a gold electrode surface $S_{16}$.

In other examples, the electrode surface $S_{16}$ may be modified to incorporate a functional group (i.e., a linking molecule) that can bind to the primer 24. The functional group is capable of chemically attaching, at one end, to the electrode surface $S_{16}$, and at the other end, to the primer 24. As examples, thiol or thiolate linkers or amine linkers may attach to gold electrodes, and silane linkers (e.g., azido silane) may attach to ITO electrodes. While some examples have been provided, it is to be understood that other chemical functionalities may be used.

Whether direct or indirect (e.g., though a linker), the attachment of the primer 24 to the electrode surface $S_{16}$ may be through covalent bonding, coordination bonding, or another chemical or physical bond (such as pi-pi stacking), depending upon the primer 24, any linker that is used, and the electrode material.

Because the surface $S_{16}$ is modified with functional groups or is inherently functionalized and the interstitial regions 22 do not include the primer-reactive functional groups, the primers 24 will attach to the surface $S_{16}$ and will not attach to the interstitial regions 22.

It is to be understood that electrode functionalization may be performed before or after the patterned material 18 is applied thereto.

In other examples, the electrode surface $S_{16}$ may be functionalized with a polymer layer as described herein in reference to FIG. 1C.

As shown in FIG. 1B, primer(s) 24 is/are attached to the functionalized electrode surface $S_{16}$. The primer 24 may be any forward amplification primer or reverse amplification primer that includes a functional group that can attach to the surface $S_{16}$, either directly to the electrode material or to a functional group attached thereto or to a polymer layer attached thereto. Examples of suitable functional group terminated primers include an alkyne terminated primer, a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, and a triazolinedione terminated primer. A mixture of primers may also be used. Specific examples of suitable primers include P5 and/or P7 primers, which are used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, GENOME ANALYZER™, and other instrument platforms.

In an example, the primers 24 may be attached using a grafting process, such as flow through deposition (e.g., when the flow cell 10 has a lid bonded thereto), dunk coating, spray coating, puddle dispensing, or by another suitable method that will attach the primer(s) 24. Each of these example techniques may utilize a primer solution or mixture, which may include the primer(s), water, a buffer (e.g., a salt solution), and a catalyst.

Referring now to FIG. 1C, the flow cell 10 includes a substrate 14 and a patterned electrode 26 positioned on the substrate 14. In this example, the patterned electrode 26 defines depressions 20 separated by interstitial regions 22. In this example, a functionalized surface S14 of the substrate 14 is exposed at each of the depressions 20, and a primer 24 is grafted to the functionalized surface S14.

The substrate 14 in FIG. 1C provides support for the other components of the flow cell 10. The substrate 14 may be any of the examples described herein.

In FIG. 1C, the patterned electrode 26 is positioned on the substrate 12. The patterned electrode 26 may be any of the electrode materials mentioned for the electrode 16. In this example, the patterned electrode 26 may be a preformed grid that is attached to the substrate 14, e.g., using an adhesive, or may be deposited on the substrate 14 in a desirable pattern using a suitable deposition technique.

In the example shown in FIG. 1C, the patterned electrode 26 includes the depressions 20 defined therein, and interstitial regions 22 separating adjacent depressions 20. Any of the patterns, layouts, and dimensions set forth herein for the depressions 20 in FIG. 1B may be used for the depressions 20 shown in FIG. 1C.

Also in the example shown in FIG. 1C, the surface $S_{14}$ of the substrate 14 exposed at the depressions 20 is functionalized so that primers 24 can attach to the surface $S_{14}$ and not to the interstitial regions 22 of the patterned electrode 26.

In some examples, functionalizing the substrate surface $S_{14}$ involves silanizing the surface $S_{14}$ exposed at the depressions 20 and forming a polymer layer on the silanized surface. Silanization may be accomplished using any silane or silane derivative. Example silane or silane derivatives include norbornene silane, a norbornene derivative (e.g., [(5-bicyclo[2.2.1]hept-2-enyl)ethyl]trimethoxysilane), a cyclooctyne, a cyclooctyne derivative, or another suitable silane. The method used to attach the silane or silane derivative may vary depending upon the silane or silane derivative that is being used. Examples of suitable silanization methods include vapor deposition (e.g., a YES method), spin coating, or other deposition methods.

A polymer (not shown) may then be applied to the silanized surface. The polymer may be a semi-rigid polymeric material that is permeable to liquids and gases. An example of the polymer includes an acrylamide copolymer, such as poly(N-(5-azidoacetamidylpentyl)acrylamide-co-acrylamide, PAZAM. PAZAM and some other forms of the acrylamide copolymer are represented by the following structure (I):

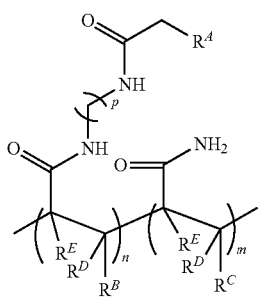

wherein:

$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;

$R^B$ is H or optionally substituted alkyl;

$R^C$, $R^D$, and $R^E$ are each independently selected from the group consisting of H and optionally substituted alkyl;

each of the —$(CH_2)_p$— can be optionally substituted;

p is an integer in the range of 1 to 50;

n is an integer in the range of 1 to 50,000; and m is an integer in the range of 1 to 100,000.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of the PAZAM may range from about 10 kDa to about 1500 kDa, or may be, in a specific example, about 312 kDa. In some examples, PAZAM is a linear polymer. In some other examples, PAZAM is a lightly cross-linked polymer.

In other examples, the polymer may be a variation of the structure (I). In one example, the acrylamide unit may be replaced with N,N-dimethylacrylamide

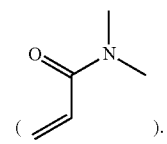

In this example, the acrylamide unit in structure (I) may be replaced with

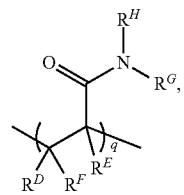

where $R^D$, $R^E$, and $R^F$ are each H or a C1-C6 alkyl, and $R^G$ and $R^H$ are each a C1-C6 alkyl (instead of H as is the case with the acrylamide). In this example, q may be an integer in the range of 1 to 100,000. In another example, the N,N-dimethylacrylamide may be used in addition to the acrylamide unit. In this example, structure (I) may include

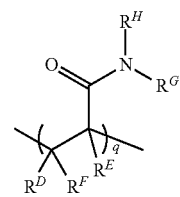

in addition to the recurring "n" and "m" features, where $R^D$, $R^E$, and $R^F$ are each H or a C1-C6 alkyl, and $R^G$ and $R^H$ are each a C1-C6 alkyl. In this example, q may be an integer in the range of 1 to 100,000.

It is to be understood that other molecules may be used to form the polymer, as long as they are functionalized to interact with the activated surface $S_{14}$ and the subsequently applied primer(s) 24. Other examples of suitable polymers include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable polymers include mixed copolymers of acrylamides and acrylates.

The polymer (e.g., PAZAM) may be deposited using spin coating, or dipping or dip coating, or flow of the functionalized molecule under positive or negative pressure, or another suitable technique. The polymer may be present in a mixture. In an example, the mixture includes PAZAM in water or in an ethanol and water mixture.

After being coated, the mixture including the polymer may also be exposed to a curing process to form the polymer across the interstitial regions 22 of the patterned electrode 26 and in the depressions 20. In an example, curing may take place at a temperature ranging from room temperature (e.g., about 25° C.) to about 95° C. for a time ranging from about 1 millisecond to about several days. In another example, the time may range from 10 seconds to at least 24 hours. In still another example, the time may range from about 5 minutes to about 2 hours.

The attachment of the polymer 20 to the silanized surfaces $S_{14}$ may be through covalent bonding. Covalent linking is helpful for maintaining at least the primer(s) 24 in the depressions 20 throughout the lifetime of the ultimately formed flow cell 10 during a variety of uses. The following are some examples of reactions that can take place between the activated (e.g., silanized) surfaces and the polymer.

When the silane or silane derivative includes norbornene or a norbornene derivative as the unsaturated moiety, the norbornene or a norbornene derivative can: i) undergo a 1,3-dipolar cycloaddition reaction with an azide/azido group of PAZAM; ii) undergo a coupling reaction with a tetrazine group attached to PAZAM; undergo a cycloaddition reaction with a hydrazone group attached to PAZAM; undergo a photo-click reaction with a tetrazole group attached to PAZAM; or undergo a cycloaddition with a nitrile oxide group attached to PAZAM.

When the silane or silane derivative includes cyclooctyne or a cyclooctyne derivative as the unsaturated moiety, the cyclooctyne or cyclooctyne derivative can: i) undergo a strain-promoted azide-alkyne 1,3-cycloaddition (SPAAC) reaction with an azide/azido of PAZAM, or ii) undergo a strain-promoted alkyne-nitrile oxide cycloaddition reaction with a nitrile oxide group attached to PAZAM.

When the silane or silane derivative includes a bicyclononyne as the unsaturated moiety, the bicyclononyne can undergo similar SPAAC alkyne cycloaddition with azides or nitrile oxides attached to PAZAM due to the strain in the bicyclic ring system.

In other examples, plasma ashing rather than silanization may be used to functionalize the exposed surfaces $S_{14}$ of the substrate 14 in the depressions 20. After plasma ashing, the mixture containing the polymer may be directly spin coated (or otherwise deposited) on the plasma ashed surfaces and then cured to form the polymer. In this example, plasma ashing may generate surface-activating agent(s) (e.g., —OH groups) that can adhere the polymer to the interstitial regions 22 and the exposed surfaces $S_{14}$ of the substrate 14 in the depressions 20. In these examples, the polymer is selected so that it reacts with the surface groups generated by plasma ashing.

Whether silanization or plasma ashing is used, polishing may then be performed in order to remove the polymer from the interstitial regions 22 of the patterned electrode 26. In some examples, polishing may or may not also remove the silane or silane derivative adjacent to the interstitial regions 22. When these silanized portions are completely removed, it is to be understood that the underlying patterned electrode 26 is exposed.

The polishing process may be performed with a gentle chemical slurry (including, e.g., an abrasive, a buffer, a chelating agent, a surfactant, and/or a dispersant) which can remove the thin polymer, and in some instances, at least part of the silane or silane derivative, from the interstitial regions 22 without deleteriously affecting the underlying patterned electrode 26 at those regions. Alternatively, polishing may be performed with a solution that does not include the abrasive particles.

The chemical slurry may be used in a chemical mechanical polishing system to polish the surface of the interstitial regions 22. The polishing head(s)/pad(s) or other polishing tool(s) is/are capable of polishing the polymer from the interstitial regions 22 while leaving the polymer in the depressions 20. As an example, the polishing head may be a Strasbaugh ViPRR II polishing head.

Cleaning and drying processes may be performed after polishing. The cleaning process may utilize a water bath and sonication. The water bath may be maintained at a relatively low temperature ranging from about 22° C. to about 30° C. The drying process may involve spin drying, or drying via another suitable technique.

It is to be understood that other chemicals and/or processes may also be used to functionalize the substrate surface $S_{14}$ in preparation for primer 24 attachment.

As shown in FIG. 1C, the primer(s) 24 is/are attached to the functionalized substrate surface $S_{14}$. Any of the primers 24 and methods for grafting the primers 24 disclosed herein may be used in the example shown in FIG. 1C, as long as the primer(s) 24 can be attached to the functional groups (e.g., functional groups of the polymer) at the substrate surface $S_{14}$.

The flow cell 10 includes an array of depressions 20, either in accordance with the architecture described in FIG. 1B or with the architecture described in FIG. 1C. An array 52 corresponding to the architecture shown in FIG. 1B is depicted in FIG. 3, and an array 52' corresponding to the architecture shown in FIG. 1C is depicted in FIG. 5. The flow cell 10 including the array 52 or 52' may be used in a sequencing workflow that generates, through electrochemiluminescence, fluorescence signals that are optically detected. Examples of these workflows will be described in reference to FIG. 4A through FIG. 4C and FIG. 6A through FIG. 6C.

Prior to sequencing, a template polynucleotide chain 40 that is to be sequenced may be formed on the flow cell surface using the primers 24. At the outset of template polynucleotide chain formation, library templates may be prepared from any nucleic acid sample (e.g., a DNA sample or an RNA sample). The nucleic acid sample may be fragmented into single-stranded, similarly sized (e.g., <1000 bp) DNA or RNA fragments. During preparation, adapters may be added to the ends of these fragments. Through reduced cycle amplification, different motifs may be introduced in the adapters, such as sequencing binding sites, indices, and regions that are complementary to the primers 24 in the depressions 20. The final library templates include the DNA or RNA fragment and adapters at both ends. In some examples, the fragments from a single nucleic acid sample have the same adapters added thereto.

A plurality of library templates may be introduced to the flow cell 10. Because the flow cell 10 includes an array 52 or 52' of depressions 20, multiple library templates are hybridized, for example, to one of two types of primers 24 immobilized on the electrode surface $S_{16}$ or the substrate surface $S_{14}$ in each of the depressions 20.

Cluster generation may then be performed. In one example of cluster generation, the library templates are copied from the hybridized primers 24 by 3' extension using a high-fidelity DNA polymerase. The original library templates are denatured, leaving the copies immobilized in the depressions 20. Isothermal bridge amplification or some other form of amplification may be used to amplify the immobilized copies. For example, the copied templates loop over to hybridize to an adjacent, complementary primer 24, and a polymerase copies the copied templates to form double stranded bridges, which are denatured to form two single stranded strands. These two strands loop over and hybridize to adjacent, complementary primers 24 and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. While a single template polynucleotide chain 40 is shown in the depression 20 in FIG. 4A-FIG. 4C and FIG. 6A-FIG. 6C, it is to be understood that clustering results in the formation of several template polynucleotide chains 40 in each depression 20. This example of clustering is bridge amplification, and is one example of the amplification that may be performed. It is to be understood that other amplification techniques may be used, such as the exclusion amplification (Examp) workflow (Illumina Inc.).

During sequencing, fluorescence signals are generated using electrochemiluminescence. As such, at least some of the nucleotides that are introduced to the flow cell 10 during sequencing are labeled nucleotides that include an electrochemiluminescent label. Examples of the labeled nucleotide 28A, 28B, 28C are shown in FIG. 2. Each of the labeled nucleotide 28A, 28B, 28C includes a nucleotide 30 having a 3' OH blocking group 32A, 32B, 32C, a linking molecule 34 attached to a base or a sugar of the nucleotide 30, and an electrochemiluminescent label 36 attached to the linking molecule 34.

The nucleotide 30 includes a nitrogen containing heterocyclic base, a sugar, and one or more phosphate groups. Nucleotides 30 are monomeric units of a nucleic acid sequence. In RNA, the sugar is a ribose, and in DNA, the sugar is a deoxyribose, i.e., a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of ribose or deoxyribose is bonded to N-1 of a pyrimidine or N-9 of a purine. The nucleotide 30 may be a monophosphate, or a polyphosphate form including several phosphate groups (e.g., tri-phosphate (i.e., gamma phosphate), tetra-phosphate, penta-phosphate, hexa-phosphate, etc.). A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA). In FIG. 2, the base of the nucleotide 30 is cytosine, the sugar is deoxyribose, and the phosphate is a tri- or gamma-phosphate.

In the examples disclosed herein, the nucleotide 30 has a 3' OH blocking group 32A, 32B, 32C attached thereto. The 3' OH blocking group 32A, 32B, 32C may be linked to an oxygen atom of the sugar molecule in the nucleotide 30. The 3' OH blocking group 32A, 32B, 32C may be a reversible terminator that allows only a single-base incorporation to occur in each sequencing cycle (as will be discussed further in reference to FIG. 4A-FIG. 4C and FIG. 6A-FIG. 6C). The reversible terminator stops additional bases from being incorporated into a nascent strand that is complementary to the template polynucleotide chain 40. This enables the detection and identification of a single incorporated base. The 3' OH blocking group 32A, 32B, 32C can subsequently be removed, enabling additional sequencing cycles to take place at each template polynucleotide chain 40. Examples of different 3' OH blocking groups 32A, 32B, 32C are shown in FIG. 2, including a 3'-$ONH_2$ reversible terminator (shown at 32A), a 3'-O-allyl reversible terminator (i.e., —CH=$CHCH_2$, shown at 32B), and 3'-O-azidomethyl reversible terminator (i.e., —$CH_2N_3$, shown at 32C). Other suitable reversible terminators include o-nitrobenzyl ethers, alkyl o-nitrobenzyl carbonate, ester moieties, other allyl-moieties, acetals (e.g., tert-butoxy-ethoxy), MOM (—$CH_2OCH_3$) moieties, 2,4-dinitrobenzene sulfenyl, tetrahydrofuranyl ether, 3' phosphate, ethers, —F, —$H_2$, —$OCH_3$, —$N_3$, —$HCOCH_3$, and 2-nitrobenzene carbonate.

A linking molecule 34 is attached to the purine base or a pyrimidine base of the nucleotide 30. In some examples, the linking molecule 34 includes a cleavage site, identified by the arrows (e.g., arrow 38) in FIG. 2. Some examples of suitable linking molecules 34 are shown in FIG. 2, although it is to be understood that any suitable cleavable linker may be used that can attach the electrochemiluminescent label 36 to the base or the sugar of the nucleotide. In other examples, the linking molecule 34 is not cleavable. This type of linking molecule 34 may be desirable when one-channel detection is used and the cleaving chemistry of the ECL label 36 is used to distinguish the incorporated nucleotide bases.

An electrochemiluminescence (ECL) label 36 is attached to the linking molecule 34. Any compound that can be attached to the linking molecule 34 and that can exhibit electrochemiluminescence in a fluid (e.g., an aqueous solution) may be used as the ECl label 36.

Some ECL labels 36 undergo self-annihilation, whereby the label 36 directly generates an excited state in response to an electrical potential that is swept from positive to negative. One example of this type of label is chlorpromazine. This type of label 36 does not need a co-reactant to produce ECL emission.

Other ECL labels 36 can be classified as either anodic ECL compounds or cathodic ECL compounds, depending on whether they are activated by oxidation or reduction, respectively.

An anodic ECL tagged nucleotide is oxidized under applied positive potential, which generates a radical cation that can then undergo an electron transfer reaction with a co-reactant (in this example, a reducing agent) to form a neutral excited state, which is emissive. Examples of anodic ECL labels 36 include tris (2,2'-bypyridine)ruthenium(II), 2-thianthrenecarboxylic acid, sodium 9, 10-diphenylanthracene-2-sulfonate (DPAS), the structures of which are respectively shown below:

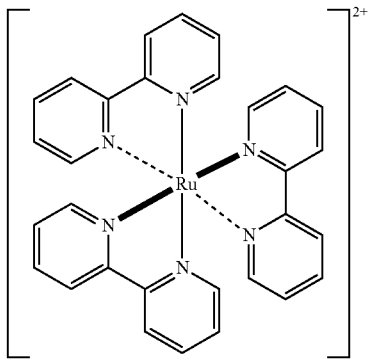

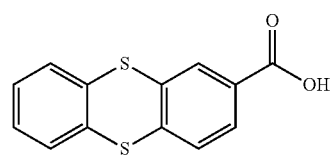

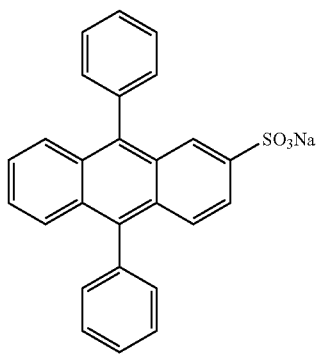

Suitable reducing agent co-reactants for anodic ECL tags include aliphatic amines, such as trialkylamines (e.g., tri-n-propylamine), and oxalate.

A cathodic ECL tagged nucleotide is reduced under applied negative potential, which generates a radical anion that can then undergo electron transfer reaction with a co-reactant (in this example, an oxidizing agent) to form a neutral excited state, which is emissive. Examples of cathodic ECL labels 36 include 3,4,9,10-perylenetetracarboxylic dianhydride and meso-tetra(4-sulfonatophenyl)porphyrin, the structures of which are respectively shown below:

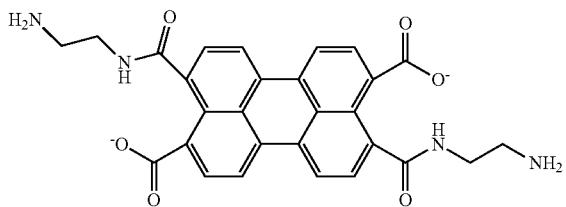

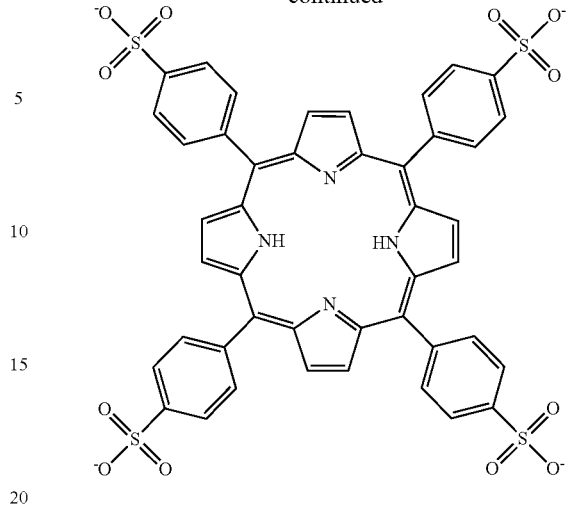

A suitable co-reactant for cathodic ECL tags includes a peroxydisulfate ($S_2O_8^{2-}$) (e.g., potassium peroxydisulfate). Sodium 9, 10-diphenylanthracene-2-sulfonate (DPAS) (shown above as an anodic ECL label) can also function as a cathodic ECL label 36, when an appropriate negative potential is applied with potassium peroxydisulfate as the co-reactant.

While several example ECL labels 36 and co-reactants have been provided, it is to be understood that other ECL labels 36 and co-reactants may be used.

Methods for sequencing using the labeled nucleotides 28A, 28B, 28C and optical detection will now be described in reference to FIG. 4A-FIG. 4C and FIG. 6A-FIG. 6C. FIG. 4A-FIG. 4C depict the method using the flow cell architecture of FIG. 1B and the array 52 of FIG. 3, and FIG. 6A-FIG. 6C depict the method using the flow cell architecture of FIG. 1C and the array 52' of FIG. 5.

Prior to a sequencing cycle, the 3'-ends of the template polynucleotide chains/strands 40 and any flow cell-bound primers 24 (not attached to the template polynucleotide chains/strands 40) may be blocked to prevent interference with the sequencing reaction, and in particular, to prevent undesirable priming.

As shown in FIG. 4A and FIG. 6A, a sequencing primer 53 may be introduced to the flow cell 10, where it will hybridize to a complementary sequence on an adapter of the template polynucleotide chain 40. This renders the template polynucleotide chain 40 ready for sequencing.

The sequencing method includes introducing a fluid (e.g., an aqueous solution) including a polymerase 42 and nucleotides (e.g., labeled nucleotide 28) to a flow cell 10 including an electrode 16 or 26 that partially defines a depression 20 including a template polynucleotide chain 40 attached in the depression 20, wherein at least some of the nucleotides are labeled nucleotides 28 as described herein. Any high or low processivity polymerase 42 may be used. Some examples include Phi29, *Bacillus stearothermophilus* (Bst), and Klenow fragment (KF), although other may be used. In addition to the polymerase(s) 42 and the labeled nucleotide(s) 28, the fluid may also include water, buffer, non-labeled nucleotides, etc. Example buffers include Tris buffer, saline-sodium citrate (SSC) buffer, ammonium sulfate buffer, phosphate buffer, etc. In some examples, the buffer may be another salt cation, such as potassium, magnesium, manganese, or others.

One of the nucleotides is incorporated, by a respective polymerase 42, into a nascent strand that extends the sequencing primer 53 and that is complementary to the template polynucleotide chain 40. In other words, at each template polynucleotide chain 40 across the flow cell 10, respective polymerases 42 extend the hybridized sequencing primer 53 by one of the nucleotides (labeled or not) in the solution. The nucleotides in solution are present as single, separate molecules, and thus natural competition minimizes incorporation bias. In FIGS. 4B and 6B, the incorporated nucleotide is the ECL labeled nucleotide 28.

In the examples disclosed herein, both the labeled nucleotides 28 and any non-labeled nucleotides include a reversible terminator. As such, incorporation of a labeled nucleotide 28 or a non-labeled nucleotide into the nascent strand serves as a terminator for polymerization. This enables electrochemical signal generation and detection to take place.

After incorporation, the fluid, which includes any non-incorporated nucleotides, may be removed from the flow cell 10. This may be accomplished using a washing solution (e.g., water).

After incorporation and removal of any non-incorporated nucleotides, the method includes applying a potential to the electrode 16 (FIG. 4B-FIG. 4C) or to the patterned electrode 26 (FIG. 6B-FIG. 6C), and detecting an optical emission 54 in response to the applied potential (FIG. 4C and FIG. 6C). The potential that is applied to the electrode 16 or to the patterned electrode 26 is sufficient to drive the ECL reaction of any labeled nucleotide 28 that has its base incorporated into the nascent strand. In some examples, a series of different potentials may be applied sequentially in order to drive the ECL reactions of different ECL labels 36.

In some examples, the potential is swept from positive to negative, which directly generates the excited state of the ECL labels 36, resulting in the optical emission 54.

In other examples, the co-reactant is introduced in the fluid with the polymerase 42 and the nucleotides. In these examples, the applied potential initiates a redox reaction pathway that involves the label 36 and the co-reactant. As an example, the applied potential can initiate electrochemical oxidation or reduction of the ECL label 36 to generate a radical ion, which is then reduced or oxidized by the co-reactant to form an excited state. The excited state results in the optical emission 54.

In still other examples, a redox shuttle may be added with the co-reactant. A redox shuttle can move charge through the fluid to or from an active species. The redox shuttle can diffuse to the electrode surface $S_{16}$ or to the depression walls that are defined by the patterned electrode 26, and become oxidized or reduced. The oxidized or reduced redox shuttle can then diffuse to and react with the ECL label 36 to form the oxidized or reduced ECL label. The oxidized or reduced ECL label would then need to react with co-reactant to form emissive state. The redox shuttle can enable an ECL label 36 to undergo a redox event when the label 36 is not in direct physical contact with the electrode 16 or 26.

In the examples shown in FIG. 4C and FIG. 6C, the optical emission 54 is imaged using a camera to capture the emission color.

A de-blocking agent may then be introduced into the flow cell 10. The de-blocking agent may be capable of i) cleaving any cleavable linking molecules 34 from the incorporated labeled nucleotide 28 (which also removes the ECL label 36) and ii) removing the 3' OH blocking group 32A, 32B, 32C (see FIG. 2) from the incorporated labeled nucleotide 28. It is to be understood that when a non-labeled nucleotide (which does not include the ECL label 36 attached thereto) is incorporated into the nascent strand, the de-blocking agent removes the 3' OH blocking group 32A, 32B, 32C from the non-labeled nucleotide. In either example, removal of the 3' OH blocking group 32A, 32B, 32C enables a subsequent sequencing cycle to be performed. Examples of 3' OH blocking groups and suitable de-blocking agents include: o-nitrobenzyl ethers and alkyl o-nitrobenzyl carbonate that can be removed photolytically; ester moieties that can be removed by base hydrolysis; allyl-moieties that can be removed with NaI, chlorotrimethylsilane and $Na_2S_2O_3$ or with Hg(II) in acetone/water; azidomethyl which can be cleaved with phosphines, such as tris(2-carboxyethyl)phosphine (TCEP) or tri(hydroxypropyl)phosphine (THP); acetals, such as tert-butoxy-ethoxy which can be cleaved with acidic conditions; MOM ($—CH_2OCH_3$) moieties that can be cleaved with $LiBF_4$ and $CH_3CN/H_2O$; 2,4-dinitrobenzene sulfenyl which can be cleaved with nucleophiles such as thiophenol and thiosulfate; tetrahydrofuranyl ether which can be cleaved with Ag(I) or Hg(II); and 3' phosphate which can be cleaved by phosphatase enzymes (e.g., polynucleotide kinase). Other useful reversible moieties include ethers, $—F$, $—H_2$, $—OCH_3$, $—N_3$, $—HCOCH_3$, and 2-nitrobenzene carbonate, and useful de-blocking treatments include irradiation with light (e.g., to induce photocleavage), heating, exposure to chemical reactants, exposure to catalysts, exposure to electrical current (e.g., to induce electrolysis), or the like.

For ease of illustration and understanding, FIG. 4A-FIG. 4C and FIG. 6A-FIG. 6C illustrate a single sequencing cycle involving a single template polynucleotide chain 40 and the incorporation of a single labeled nucleotide 28 into a nascent strand formed complementary to the template polynucleotide chain 40. It is to be understood, however, that each depression 20 includes several (e.g., up to several million) template polynucleotide chains 40 (amplicons), and single base incorporation may simultaneously take place at each template polynucleotide chain 40 in each depression 20. Imaging will capture the emissions 54 resulting from the various incorporation events and the applied potential(s), and the respectively incorporated bases can be identified from the image. Captured images may be processed with image analysis software to determine which nucleotides were incorporated at each cluster position across the flow cell.

In the examples disclosed herein, the ECL label 36 may have a specific emission spectrum, a specific oxidation or reduction potential, a specific emission lifetime, a specific emission intensity, and/or a specific cleavage chemistry. These unique characteristics enable different ECL labels 36 to be identified, e.g., by their respective (and distinct) emissions, by respective (and distinct) potentials used to initiate oxidation or reduction, by their respective (and distinct) emission lifetimes, and/or by the presence or absence of particular cleavage activity. In an example, the respective and distinct emission, potential, emission lifetime, and/or cleavage activity of any one ECL label 36 is different from the emission, potential, emission lifetime, and/or cleavage activity of any other ECL label 36 used in a plurality of labeled nucleotides 26. As such, a specific ECL label 36 having one or more of these unique characteristics can be coupled to a particular nucleotide base (e.g., A, T, C, and G). When the labeled nucleotide 28A, 28B, 28C is incorporated into a nascent strand during sequencing, the unique characteristic of the ECL label 36 can be detected and then utilized to identify the incorporated base.

For one example, four different ECL labels with four different emission spectra (i.e., emission in four different wavelength bands) may be respectively attached to the four nucleotide bases, A, T, C, and G. During imaging in a sequencing cycle, four distinct images using the four different wavelength bands may be captured and processed to identify which nucleotides have been incorporated.

For another example, three different ECL labels with three different emission spectra (i.e., emission in three different wavelength bands) may be respectively attached to three nucleotide bases, A, T, and C, and the nucleotide base G may remain natural (i.e., not labeled). During imaging in a sequencing cycle, three distinct images using the three different wavelength bands may be captured and processed to identify which nucleotides have been incorporated. In the images, no emission (i.e., a dark response) enables the identification of the fourth nucleotide base.

For still another example, four different ECL labels 36 with four different oxidation or reduction potentials may be respectively attached to the four nucleotide bases, A, T, C, and G. During the sequencing cycle, the oxidation or reduction potential used to initiate a particular emission may be recorded with a particular image. The identification of the four bases may be achieved by correlating the emissions with the applied oxidation or reduction potentials initiating the emissions. In this example, the emission may be in the same optical channel because the oxidation or reduction potential causing the emission will be used to distinguish the signals.

In an additional example, four different ECL labels with four different emission lifetimes may be respectively attached to the four nucleotide bases, A, T, C, and G. During imaging, the different emission lifetimes may be recorded. This data enables identification of any one or more of the four different nucleotide bases.

In yet a further example, four different ECL labels with four different emission intensities may be respectively attached to the four nucleotide bases, A, T, C, and G. During imaging, the different emission intensities may be recorded. This data enables identification of any one or more of the four different nucleotide bases. In another example, three different ECL labels with three different emission intensities may be respectively attached to three nucleotide bases, A, T, and C, and the nucleotide base G may remain natural (e.g., not labeled).

For yet a further example, the same type of ECL label 36 may be coupled with linking molecules 34 having different cleaving chemistry. In this example, four different nucleotides may be used in the fluid. In an example, the fluid includes: a first labeled nucleotide 28A, 28B, 28C including a cleavable linking molecule 34 attached to the ECL label 36; a second labeled nucleotide 28A, 28B, 28C including a non-cleavable linking molecule 34 attached to the ECL label 36; a third non-labeled nucleotide having a 3' OH blocking group and including a linking molecule 34 that is capable of attaching to the ECL label 36; and a fourth non-labeled nucleotide having a 3' OH blocking group. Because one ECL label 36 (that is activated at the same potential and emits in one channel) is attached to or is attachable to several of the nucleotides in solution, two chemistry steps, two electrode potential applications, and two imaging steps are utilized per sequencing cycle. In this example, the first through fourth different nucleotides are added in the first chemistry step, the oxidation or reduction potential of the ECL label 36 is applied, and an image is taken; and then a new reagent is added in the second chemistry step that removes the ECL label 36 from the first labeled nucleotide and adds the ECL label 36 to the third non-labeled nucleotide, the oxidation or reduction potential of the ECL label 36 is applied again, and another image is taken. In this example, the first labeled nucleotide is imaged in the first image only because its ECL label 36 is removed before the second image is taken; the second labeled nucleotide is imaged in both the first and second images because its ECL label 36 is permanently attached; the third non-labeled nucleotide is imaged in the second image only because the ECL label 36 is introduced and attached after the first image is taken; and the fourth non-labeled nucleotide is permanently dark because it does not include the ECL label 36 or have the ECL label 36 introduced thereto. In this example, the different nucleotides are identified by analysis of the different emission patterns for each base across the two images.

The sequencing cycles can be repeated to determine the sequence of bases in the template polynucleotide chain 40, one base at a time.

While optical detection of the electrochemically generated signals has been described, it is to be understood that examples of the flow cell architecture shown in FIG. 1B and FIG. 1C can also be integrated with a complementary metal-oxide semiconductor (CMOS), so that the ECL generated fluorescence signals (optical emissions 54) are electrically detected. FIG. 7 illustrates the flow cell architecture shown in FIG. 1B integrated with a CMOS (detection device 44), and FIG. 8 illustrates the flow cell architecture shown in FIG. 1C integrated with a CMOS (detection device 44).

In the example flow cell 10' shown in FIG. 7, the electrode 16 is transparent; the substrate 14 is transparent; and a detection device 44 (e.g., the CMOS) is in contact with the substrate 14. The detection device 44 includes a respective photodiode 50 operatively associated with each of the depressions 20; and device circuitry electrically connected to the respective photodiode 50.

Figure 8:
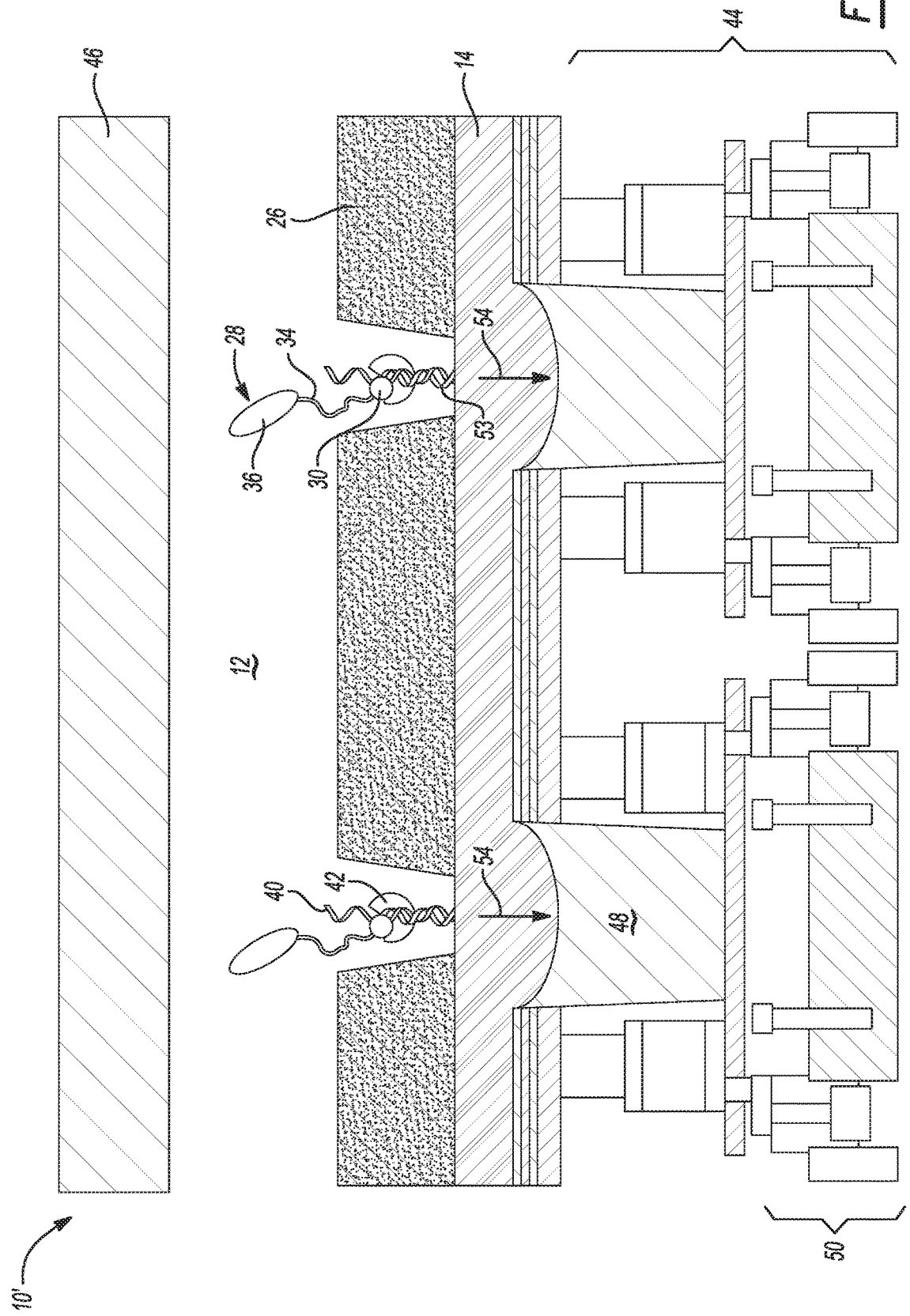
FIG. 8 is a cross-sectional view of another example of a flow cell for a sequencing kit, where the flow cell incorporates a CMOS detection device.

In the example flow cell 10' shown in FIG. 8, the substrate 14 is transparent; and a detection device 44 (e.g., the CMOS) is in contact with the substrate 14. The detection device 44 includes a respective photodiode 50 operatively associated with each of the depressions 20; and device circuitry electrically connected to the respective photodiode 50.

In the examples shown in FIG. 7 and FIG. 8, the term "transparent" means that the transparent electrode and/or the transparent substrate allow(s) the light emissions 54 to pass therethrough. Moreover, the transparent substrate may be similar to a passivation layer in a CMOS device.

The detection devices 44 in these examples are CMOS devices that include a plurality of stacked layers including, for example, silicon layer(s), dielectric layer(s), metal-dielectric layer(s), metal layer(s), etc.). The stacked layers make up the detection circuitry. The detection circuitry 44 may include interconnected conductive elements (e.g., conductors, traces, vias, interconnects, etc.) that can conduct electrical current. The circuitry may be configured for selectively transmitting data signals that are based on detected photons. The circuitry may also be configured for signal amplification, digitization, storage, and/or processing. The circuitry may collect and analyze the detected light emissions 54 and generate data signals for communicating the detection data. The circuitry may also perform additional analog and/or digital signal processing in the detection device 44.

The detection device 44 also includes optical components, such as the photodiode 50 (or other optical sensor(s)) and an optical waveguide(s) 48. In the examples shown in FIGS. 7 and 8, the optical components are arranged such that each photodiode 50 at least substantially aligns with, and thus is operatively associated with, a single optical waveguide 48 and single depression 20.

As used herein, the photodiode 50 may be a light sensor that includes one pixel or more than one pixel. As an example, each photodiode 50 may have a detection area that is less than about 50 µm². As another example, the detection area may be less than about 10 µm². As still another example, the detection area may be less than about 2 µm². In the latter example, the photodiode 50 may constitute a single pixel. An average read noise of each pixel the photodiode 50 may be, for example, less than about 150 electrons. In other examples, the read noise may be less than about 5 electrons. The resolution of the optical sensor(s) 18 may be greater than about 0.5 megapixels (Mpixels). In other examples, the resolution may be greater than about 5 Mpixels, or greater than about 10 Mpixels.

Also as used herein, the single optical waveguide 48 may be a light guide including a material that permits the light emissions 54 to propagate therethrough toward corresponding photodiodes 50. Because the methods disclosed herein generate the optical emissions 54 electrochemically, the material in the optical waveguide 48 does not need to be a filter for excitation light. An example of a suitable light guide material is an oxide. The light guide material may be surrounded by a dielectric or metal material that helps form the light-guiding structure.

For the flow cells 10' shown in FIG. 7 and FIG. 8, the sequencing methods may be performed as described herein in reference to FIG. 4A-FIG. 4C and FIG. 6A-FIG. 6B. The detection device 44 is also a solid state imager, and thus can image the optical emission 54 in accordance with the examples disclosed herein. In additional, light emissions 54 are detected by the photodiodes 50 of the detection device 44. The photodiodes 50 can detect the photons of the light emission 54, and convert these signals into electrical signals (e.g., electrical current or voltage). The electrical signals correlate with the optical emission of the various ECL labels 36 and thus can be used for identification of the single base incorporation events.

While not shown in FIG. 7 and FIG. 8, it is to be understood that the flow cells 10' may include two controllers so that electrochemical generation of the optical emission 54 is orthogonal to the sensing of optical emission 54. In other words, the potential(s) applied to the electrode 16 or the patterned electrode 26 can be controlled separately from the circuitry of the detection device 44.

It is also noted that a lid 46 is shown in FIG. 7 and FIG. 8. The lid 46 may be used in any of the examples disclosed herein to create the flow channel(s) 12 of the flow cells 10, 10'. In the examples shown in FIG. 1A, and FIG. 3 through FIG. 6C, the lid 46 may be a transparent material, so that the optical emission 54 can be received by a detector. In FIG. 7 and FIG. 8, the lid 46 may be made of any material since there is no excitation source and the optical emission 54 is guided through the detection device 44 to the photodiode 50.

The examples disclosed herein generate unique and distinguishable signals electrochemically, and thus eliminate the need for an excitation source. This simplifies the overall sequencing systems that can be used with the flow cells 10, 10' disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Furthermore, it is to be understood that the ranges provided herein include the stated range and any value or sub-range within the stated range, as if they were explicitly recited. For example, a range represented by from about 2 mm to about 300 mm, should be interpreted to include not only the explicitly recited limits of from about 2 mm to about 300 mm, but also to include individual values, such as about 5 mm, 222.5 mm, 275 mm, etc., and sub-ranges, such as from about 150 mm to about 180 mm, etc.

While several examples have been described in detail, it is to be understood that the disclosed examples may be modified. Therefore, the foregoing description is to be considered non-limiting.

What is claimed is:

1. A flow cell, comprising:
   a substrate consisting of a material selected from the group consisting of epoxy siloxane, glass, modified glass, nylon, ceramics/ceramic oxides, silica (silicon oxide $SiO_2$), fused silica, silica-based materials, aluminum silicate, silicon nitride ($Si_3N_4$), and inorganic glasses;
   a lid;
   a flow channel defined between the lid and the substrate;
   a patterned electrode directly positioned on the substrate and in the flow channel, wherein the patterned electrode has walls that define depressions in the flow channel, wherein the substrate defines a bottom of the depressions, wherein the depressions are separated by interstitial regions, and wherein the interstitial regions are defined by a surface of the patterned electrode that is exposed to the flow channel;
   a functionalized surface of the substrate exposed at the bottom of each of the depressions, the functionalized surface including a polymer layer attached to silane groups or hydroxyl groups attached to the substrate; and
   a primer grafted to a functional group of the polymer layer in each of the depressions.

2. The flow cell as defined in claim 1, wherein:
   the substrate is transparent; and
   the flow cell further comprises:
      a detection device in contact with the substrate, the detection device including:
         a respective photodiode operatively associated with each of the depressions; and
         device circuitry electrically connected to the respective photodiode.

3. The flow cell as defined in claim 1, wherein the polymer layer has the structure:

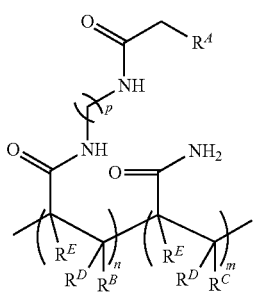

and wherein:
- $R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
- $R^B$ is H or optionally substituted alkyl;
- $R^C$, $R^D$, and $R^E$ are each independently selected from the group consisting of H and optionally substituted alkyl;
- each of the $-(CH_2)_p-$ can be optionally substituted;
- p is an integer in the range of 1 to 50;
- n is an integer in the range of 1 to 50,000; and
- m is an integer in the range of 1 to 100,000.

4. The flow cell as defined in claim 1, wherein the primer includes two types of amplification primers, and wherein the two types of amplification primers are to amplify a respective library template in each of the depressions through bridge amplification.

5. A sequencing kit, comprising:
the flow cell as defined in claim 1; and
labeled nucleotides to be introduced into the flow cell, each labeled nucleotide including:
a nucleotide having a 3' OH blocking group;
a linking molecule attached to a base or a sugar of the nucleotide; and
an electrochemiluminescent label attached to the linking molecule.

6. The sequencing kit as defined in claim 5, wherein the labeled nucleotides include at least three different labeled nucleotides, and wherein a respective electrochemiluminescent label of each of the at least three different labeled nucleotides has a distinct emission spectrum.

7. The sequencing kit as defined in claim 5, wherein the labeled nucleotides include at least three different labeled nucleotides, and wherein the electrochemiluminescent label of each of the at least three different labeled nucleotides has a distinct oxidation or reduction potential.

8. The sequencing kit as defined in claim 5, wherein the labeled nucleotides include at least three different labeled nucleotides, and wherein a respective electrochemiluminescent label of each of the at least three different labeled nucleotides has a distinct lifetime for electrochemiluminescence emission.

9. The sequencing kit as defined in claim 5, wherein the labeled nucleotides include at least three different labeled nucleotides, and wherein a respective electrochemiluminescent label of each of the at least three different labeled nucleotides has a distinct electrochemiluminescence emission intensity.

10. The sequencing kit as defined in claim 5, wherein the electrochemiluminescent label is selected from the group consisting of chlorpromazine, tris (2,2'-bypyridine)ruthenium(II), 2-thianthrenecarboxylic acid, sodium 9, 10-diphenylanthracene-2-sulfonate, 3,4,9,10-perylenetetracarboxylic dianhydride and meso-tetra(4-sulfonatophenyl)porphyrin.

* * * * *

UNITED STATES PATENT AND TRADEMARK OFFICE
CERTIFICATE OF CORRECTION

| | | |
|---|---|---|
| PATENT NO. | : 11,841,310 B2 | Page 1 of 1 |
| APPLICATION NO. | : 16/701863 | |
| DATED | : December 12, 2023 | |
| INVENTOR(S) | : Hayden Black and Brian D. Mather | |

It is certified that error appears in the above-identified patent and that said Letters Patent is hereby corrected as shown below:

In the Claims

Column 26, Line 31:
In Claim 10, delete "bypyridine)" and insert -- bipyridine) --.

Signed and Sealed this
Twenty-second Day of October, 2024

Katherine Kelly Vidal
*Director of the United States Patent and Trademark Office*